United States Patent [19]

Moeschler et al.

[11] Patent Number: 4,552,954

[45] Date of Patent: Nov. 12, 1985

[54] CONCENTRATING NIKKOMICIN MIXTURES

[75] Inventors: Heinrich-Ferdinand Moeschler, Cologne; Christian Gölker, Wuppertal; Peter M. Lange, Leverkusen, all of Fed. Rep. of Germany

[73] Assignee: Bayer Aktiengesellschaft, Leverkusen, Fed. Rep. of Germany

[21] Appl. No.: 497,433

[22] Filed: May 26, 1983

Related U.S. Application Data

[63] Continuation of Ser. No. 265,049, May 19, 1981, abandoned.

[30] Foreign Application Priority Data

May 31, 1980 [DE] Fed. Rep. of Germany ....... 3020722

[51] Int. Cl.$^4$ ........................................... C07H 17/00
[52] U.S. Cl. ................................................... 536/24
[58] Field of Search ........................................... 536/24

[56] References Cited

U.S. PATENT DOCUMENTS

| | | | |
|---|---|---|---|
| 4,287,186 | 9/1981 | Zähner et al. | 536/24 |
| 4,315,922 | 2/1982 | Hagenmaier et al. | 424/180 |
| 4,402,947 | 9/1983 | Moeschler et al. | 536/24 |

*Primary Examiner*—Ethel G. Love
*Attorney, Agent, or Firm*—Sprung Horn Kramer & Woods

[57] ABSTRACT

A process for concentrating nikkomicins (X) and (Z) from a dilute impure aqueous solution thereof, comprising contacting the solution with a weakly basic ion exchanger and eluting the adsorbed material with an acid thereby to obtain a concentrated mixture of nikkomicin (X) and nikkomicin (Z). The dilute solution being treated can directly be a filtered microbial cultivation liquor or such a liquor can be prepurified by contact with an acid ion exchanger followed by elution with a base. The recovered material is of relatively high purity.

12 Claims, No Drawings

CONCENTRATING NIKKOMICIN MIXTURES

This application is a continuation of application Ser. No. 265,049, filed May 19, 1981, now abandoned.

The present invention relates to a new unobvious process for the preparation of concentrated nikkomicin mixtures. (This compound is also known as Nikkomycin.

Nikkomicin, its preparation by a microbiological route by means of the strain Streptomyces tendae Ettlingen (CBS 354.75) and its use as a plant protection agent are known (see German Offenlegungsschrift (German Published Specification) No. 2,537,028 and U.S. Pat. Nos. 4,046,881 and 4,158,608).

It has been found that the nikkomicin obtained in this manner is a mixture of substances which resemble one another and are called nikkomicins. The main components of the nikkomicin mixtures obtained from the fermentation and working up correspond to the general formula

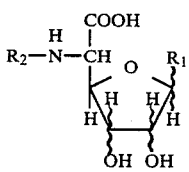
(I)

in which

R$_1$ denotes

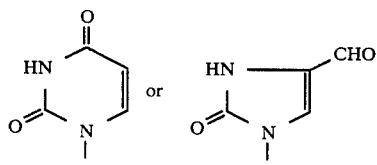

or and

R$_2$ denotes

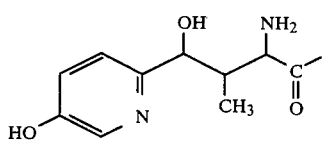

Nikkomicins are valuable agents for combating plant pests and can be used, for example, as insecticides, in particular acaricides, or fungicides.

The invention relates to a new process for concentrating the nikkomicins, which are referred to as nikkomicin (X) and nikkomicin (Z) and which are of the following formulae:

Nikkomicin (X)

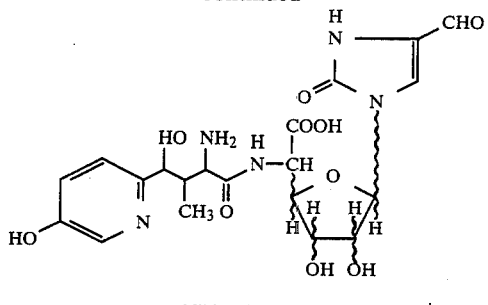

Nikkomicin (Z)

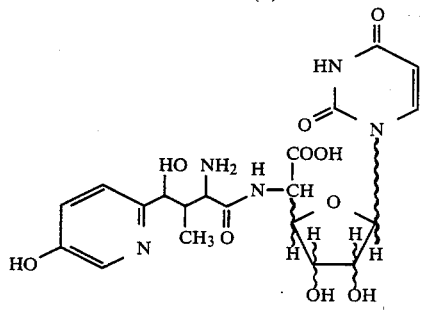

Nikkomicin (X) and nikkomicin (Z) and their mixtures have proved to be of particular importance.

It has already been disclosed, in the abovementioned patents, to concentrate nikkomicin by a procedure in which, in a first stage, the culture filtrate obtained in the fermentation is acidified to pH 4.0 with acetic acid and treated with the neutral form of an acid ion exchanger and then eluted with dilute ammonia and the solution thus obtained is concentrated and, in a second stage, the concentrate containing nikkomicin is subsequently acidified to pH 4.0 with acetic acid and treated with the neutral form of another weakly acid ion exchanger and then eluted with dilute ammonia, and the solution thus obtained is concentrated and, in a third stage, the concentrate containing nikkomicin is subsequently acidified to pH 4.0 with acetic acid and treated with SP-"Sephadex" C-25 (Trade Mark of Messrs. Pharmacia Fine Chemicals, Uppsala, Sweden) and then eluted with pyridine/acetate buffer, and the solution thus obtained is concentrated and, finally, in a fourth stage, the concentrate is treated with "Bio-Gel" P-2 (Trade Mark of Bio-Rad Laboratories, Richmond, Cal. USA) and eluted with water and the solution thus obtained is lyophilised.

Because it comprises four stages, the process is very expensive and not completely satisfactory for industrial purposes.

According to the present invention we provide a process for concentrating nikkomicins (X) and (Z) from a culture filtrate obtained from the production of nikkomicin by a microbial route or from crude nikkomicin, in which the culture filtrate or the crude nikkomicin (optionally after having been prepurified by adsorption onto an acid ion exchanger and elution with a weak base, and optionally subsequently isolated) is treated, in aqueous solution, with a weakly basic ion exchanger and eluted with an acid and the mixture of nikkomicin (X) and nikkomicin (Z) is isolated. The pair of nikkomicin components (X) and (Z) can be concentrated in a simple manner and with a high selectivity by the process of the present invention.

It is decidedly surprising that the pair of nikkomicin components (X) and (Z) remains unchanged in the adsorption, according to the invention, of the mixture of nikkomicin (X) and (Z) on the basic ion exchanger, even though it has already been known for a long time that nikkomicins are decidedly unstable to alkali. According to the state of the art, it was to be expected that nikkomicin would be hydrolyzed on the basic ion exchanger and the desired product thus would not be obtained.

As already stated above, a very good concentration of the nikkomicin (X) and (Z) is achieved by the new process. The degree of concentration depends, of course, on the type of starting material and on the type and amount of basic ion exchanger used and of the eluting agent.

The type and nature of the crude nikkomicin which can be used according to the invention are, to a very large extent, not critical. The crude nikkomicin can be used in a prepurified form or in the non-prepurified form in which it is obtained when produced by a microbial route, after being isolated or in the form of a solution, such as is obtained when the culture broth is worked up. The crude nikkomicin (if it is in the isolated form) should as far as possible contain at least 0.5%, preferably at least 10% and very particularly preferably 20 to 30%, of the mixture of nikkomicins (X) and (Z) (the percentages by weight relate to the dry mass). For example, the nikkomicin obtained according to German Offenlegungsschrift (German Published Specification) No. 2,537,028 or the corresponding U.S. Pat. Nos. 4,046,881 and 4,158,608, can be used.

In a preferred embodiment of the invention, the culture filtrate obtainable after the fermentation (see the abovementioned patents) can be used directly, without further working up. This procedure is distinguished by a particular simplicity.

In another preferred embodiment of the invention, the culture filtrate obtained after the fermentation is treated with an acid ion exchanger in a first step. On subsequent elution with dilute ammonia, a crude nikkomicin solution is obtained, which is particularly suitable for concentration of the nikkomicins (X) and (Z) by the process according to the invention.

If the crude nikkomicin is not already in the form of a solution, or if a culture filtrate is employed, the crude nikkomicin is dissolved in, preferably, demineralized or distilled water in order to carry out the process according to the invention. The concentration of the solution is not critical and is limited only by the solubility of the nikkomicin on the one hand and, on the other, by the desire for an amount of liquid which can easily be handled (a function of the dimensions of the equipment to be used). If it does not already have an appropriate pH value, the solution of crude nikkomicin is generally brought to a pH value of between about 4 and 7, preferably about 6 to 7, by adding acid. All the customary inorganic acids (for example HCl) and, preferably, organic acids, in particular lower aliphatic carboxylic acids, such as acetic acid or propionic acid, which do not attack nikkomicin can be used for this. Acetic acid is preferred.

The aqueous solution (which can also contain organic solvents, such as methanol) is brought into contact with the basic ion exchanger in the customary manner (for example by discharging onto a column or by stirring with the ion exchanger in a kettle). The most advantageous amount of ion exchanger depends on the solution employed and on the type of ion exchanger and can easily be determined by customary methods.

Any of the customary basic ion exchangers can be used for carrying out the process according to the invention. Examples which may be mentioned are: basic macroporous or gel-like polystyrene resins which are crosslinked with divinylbenzene and which are partly or completely substituted by primary, secondary, tertiary or quaternary nitrogen groups. It is also possible to use macroporous and gel-like ion exchangers which are derived from crosslinked polyacrylamide.

Basic gel-like or macroporous ion exchangers which are based on acrylates or methacrylates and have been trans-amidated with, for example, dimethylaminopropylamine can also be used. The functional nitrogen can be in the form of primary groupings, secondary groupings, tertiary groupings or quaternary groupings or as a mixture of these groupings. A macroporous amino-methylated polystyrene crosslinked with about 6% of divinylbenzene (see German Patent Specification No. 2,418,976 and U.S. Pat. No. 3,989,650) is particularly preferred as the weakly basic ion exchanger.

Basic gel-like ion exchangers based on dextran can also be employed, according to the invention, as basic ion exchangers.

Specific examples of basic ion exchangers which may be mentioned are: "Lewatit" MP 500 (Trade Mark of BAYER AG, Leverkusen, Germany (FRG), "Dowex" MSA-1 (Trade Mark of Dow Chemicals, USA) and DEAE-"Sephadex" A-25 and QAE-"Sephadex" A 25 (Trade Marks of Pharmacia, Uppsala, Sweden).

The loaded ion exchanger is then preferably washed once or several times with water.

Acids which are suitable for eluting the pair of nikkomicin components (X)+(Z) from the basic ion exchanger are dilute solutions of 10 aliphatic carboxylic acids, for example acetic acid, which can easily be removed in a simple manner, for example by evaporation or by entraining with other suitable solvents, without the pH value thereby being altered to such a great extent towards an acid medium that hydrolysis of the pair of nikkomicin components (X)+(Z) occurs. The concentration is preferably in the range from about 0.1 to 10%, in particular about 1 to 5% (% by weight).

The elution of the mixture of nikkomicin (X) and nikkomicin (Z) can be carried out by the generally customary methods, for example by simple stirring with solutions of increasing acid concentration (preferably using acetic acid), or by gradient elution over a column.

When the basic ion exchanger loaded with the mixture of nikkomicin (X) and nikkomicin (Z) is stirred with solutions of increasing acid concentration, preferential concentration of nikkomicin (Z) is achieved in the first fractions, while chiefly nikkomicin (X) is concentrated later, at higher acid concentrations.

The ratio of nikkomicin (X) to nikkomicin (Z) in the mixture can thus be greatly influenced, as desired, by separating off the particular corresponding fractions.

The mixture of nikkomicins (X) and (Z) is isolated from the eluate by the methods generally customary in biochemistry, for example by evaporating off the solvent, preferably under reduced pressure, or by freeze-drying.

For completeness, it should be pointed out that the process according to the invention can also be carried out several times in succession.

As has already been stated above, in preferred embodiments of the invention, it is possible for a culture filtrate from the microbial production to be used directly as the starting material. Alternatively the nikkomicin solution may be concentrated in a preliminary stage by treating the culture filtrate or crude nikkomicin with an acid ion exchanger, with subsequent elution with a weak base. This step will be described in more detail below.

The culture filtrate obtained in a known manner in the production of nikkomicin by a microbial route is generally adjusted to a pH value of 2 to 5, preferably 3.5 to 4.5 and in particular 4, by adding acid. Suitable acids here are those acids which are capable of establishing the above pH values. Lower aliphatic carboxylic acids, in particular acetic acid, are preferably used.

This solution is treated with an acid ion exchanger by generally customary methods.

The nikkomicin (X) and (Z) can be bonded, for example by simply striking them with the ion exchanger or by discharging the nikkomicin solution onto, or allowing it to flow through, a column filled with ion exchanger.

Suitable acid ion exchangers are, preferably, the customary macroporous or gel-like ion exchangers of polystyrene resins which are crosslinked with divinylbenzene and have sulphonic acid groupings, for example "Lewatit" SC 104 (Trade Mark of BAYER AG, Leverkusen, Germany (FRG) and "Dowex" 50 WX 4 (Trade Mark of Dow Chemicals, USA).

The loaded ion exchanger is preferably washed once or several times with water.

Weak bases, for example dilute ammonia, are suitable for eluting the pair of nikkomicin components (X) and (Z) from acid ion exchangers. The concentration is preferably in the range from 0.01N to 0.1N, in particular 0.04 to 0.06N.

The eluate or a solution of the crude nikkomicin isolated from the eluate is brought to the required pH value, as described above, and treated with the basic ion exchanger.

The process according to the invention will be illustrated by the following examples. The yields were in each case determined by HPLC (High Pressure Liquid Chromatography). The yield data in each case relate to the content of the mixture in the crude nikkomicin employed. The end product was in each case obtained from the solution by lyophilization. The weakly basic ion exchanger employed in Examples 3 to 6 is a macroporous amino-methylated polystyrene crosslinked with 6% of divinylbenzene (see German Patent Specification No. 2,418,976 and U.S. Pat. No. 3,989,650). Before use, the ion exchanger was in each case washed with water and adjusted to pH 7.0 with acetic acid. Unless indicated otherwise, the % data relate to % by weight.

EXAMPLE 1

Gradient elution 100 g of crude nikkomicin [about 15% of nikkomicin (X)+(Z)] were dissolved in 400 ml of demineralized water and the pH value of the solution was adjusted to 6.5 to 7.0 with acetic acid. This solution was added to 1 kg of the basic ion exchanger "Lewatit" MP 500 (polystyrene resin crosslinked with divinylbenzene and containing quaternized amino groups) in the acetate form (washed with $H_2O$), suspended in 1,600 ml of demineralized water, and pH value of the solution being kept at 6.5 to 7.0 and the mixture being stirred for 1 hour. The ion exchanger was filtered off, packed into a column (60 cm×7.5 cm$\phi$) and washed with demineralized water until the eluate was colorless. The column was eluted with a linear gradient, using 4.5 liters of demineralized water and 4.5 liters of 10% strength acetic acid. About 60 to 70% strength nikkomicin (x)−(Z) was obtained in a yield of 65%.

EXAMPLE 2

Stepwise elution in a batch process 1 kg of crude nikkomicin [about 15% of nikkomicin (X)+(Z)] was dissolved in 4 liters of demineralized water and the pH value of the solution was adjusted to 6.5 to 7.0 with acetic acid. This solution was added to 10 kg of the basic ion exchanger "Lewatit" MP 500 (polystyrene resin crosslinked with divinylbenzene and containing quaternary amino groups) in the acetate form (washed with water), suspended in 16 liters of demineralized water, the pH value of the solution being kept at 6.5 to 7.0 and the mixture being stirred for 1 hour. Thereafter, the loaded exchanger resin was filtered off and extracted by stirring three times with in each case 10 liters of water and for in each case 15 minutes. The washed ion exchanger resin was then extracted stepwise by stirring, in each case for ½ an hour and with in each case 10 liters of acetic acid of increasing concentration (1%, 2%, 3%, 4%, 5% and 10%) the pH value being kept constant during the particular extraction stage by adding acetic acid. 50 to 70% strength nikkomicin (X)+(Z) was obtained in a yield of 70%.

EXAMPLE 3

Gradient elution 100 g of crude nikkomicin [about 20% of nikkomicin (X)+(Z)] were dissolved in 400 ml of demineralized water and the pH value of the solution was adjusted to 6.5 to 7.0 with acetic acid. This solution was added to 1 kg of weakly basic ion exchanger (washed and adjusted to pH 7.0 with acetic acid), suspended in 1,600 ml of demineralized water, the pH value of the solution being kept at 6.5 to 7.0 by adding acetic acid and the mixture being stirred for 1 hour. The ion exchanger was filtered off, packed into a column (60 cm×7.5 cm$\phi$) and washed with demineralized water until the eluate was colorless. The column was eluted with a linear gradient, using 4.5 liters of demineralized water and 4.5 liters of 10% strength acetic acid. About 70 to 75% strength nikkomicin (X)+(Z) was obtained in a yield of 65%.

EXAMPLE 4

Stepwise elution in a batch process 1 kg of crude nikkomicin [about 15% of nikkomicin (X)+(Z)] was dissolved in 4 liters of demineralized $H_2O$ and the pH value of the solution was adjusted to 6.5 to 7.0 by adding acetic acid. This solution was added to 10 kg of a weakly basic ion exchanger (washed and adjusted to pH 7.0 with acetic acid), suspended in 16 liters of demineralized water, the pH value of the solution being kept at 6.5 to 7.0 by adding acetic acid and the mixture being stirred for 1 hour. The loaded exchanger resin was then filtered off and extracted by stirring three times with in each case 10 liters of water and in each case for 15 minutes. The washed ion exchanger resin was then extracted stepwise by stirring, in each case for ½ hour and with in each case 10 liters of acetic acid of increasing concentration (1%, 2%, 3%, 4%, 5% and 10%), the pH value being kept constant during the particular extraction stage by adding acetic acid. An up to 70% strength nikkomicin (X)+(Z) was obtained in a yield of 80%.

EXAMPLE 5

Gradient elution 5 kg of crude nikkomicin (15 to 30%) were dissolved in 20 liters of demineralized water and the pH value was adjusted to 6.5 to 7.0 with acetic acid. 80 liters of demineralized water and 50 kg of weakly basic ion exchanger (washed and adjusted to pH 7.0 with acetic acid) were initially introduced into a receiver with a stirrer. The crude nikkomicin solution was added and the mixture was stirred for 60 minutes. The pH value was kept at 6.5 to 7.0 by adding the appropriate amount of acetic acid. The charged ion exchanger was washed twice with in each case 100 liters of demineralized water. The ion exchanger was then packed into a conical glass column. The column was eluted with a linear gradient, obtained from 600 liters of demineralized water and 600 liters of 10% strength acetic acid. The first runnings from the column were discarded. Elution of the nikkomicin was followed with the aid of the pH value and the conductivity.

The purity was about 90%, with a yield of 70 to 80%.

EXAMPLE 6

Stepwise elution by a batch process 5 kg of crude nikkomicin [15 to 30% of nikkomicin (X)+(Z)] were dissolved in 20 liters of demineralized water and the pH value of the solution was adjusted to 6.5 to 7.0 with acetic acid. 80 liters of demineralized water and 50 kg of weakly basic ion exchanger (washed and adjusted to pH 7.0 with acetic acid) were initially introduced into a receiver with a stirrer, and the crude nikkomicin solution was stirred in. The mixture was stirred for 60 minutes. The pH value was kept at 6.5 to 7.0 by adding acetic acid. The loaded ion exchanger was washed three times with in each case 100 liters of demineralized water.

The ion exchanger was then eluted stepwise with in each case 50 liters of acetic acid of ascending concentration (1,3,4 and 10%), the pH value being monitored and being kept constant. The purity was about 90%, with a yield of 70 to 80%.

EXAMPLE 7

Preparation of crude nikkomicin from a culture broth by adsorption with an acid ion exchanger 2,000 liters of fermentation broth (see, for example, German Offenlegungsschrift (German Published Specification) No. 2,537,028 and U.S. Pat. Nos. 4,046,881 and 4,158,608) were centrifuged using a separator and the centrifugate was adjusted to a pH value of 4.0 with acetic acid. The centrifugate was again clarified via a separator, about 2,400 liters of filtrate, including the rinsing water necessary for removing material from the drum, being obtained. This filtrate was stirred with 750 liters of a cation exchanger "Lewatit" SC 104 (based on polystyrene) in the Na+ form for 30 minutes. The supernatant liquor was drawn off by suction and the resin was washed out by stirring with 1,250 liters of demineralized water. For elution, the ion exchanger was extracted by stirring with 0.01N ammonia solution (1,125 liters) for 10 minutes. The eluate was drawn off by means of suction nozzles. The pH value of the eluate was adjusted to be between 6 and 6.8. Thereafter, the ion exchanger was extracted by stirring with 0.05N ammonia solution (1,800 liters) for 30 minutes. The supernatant liquor was likewise drawn off by suction. Thereafter, the ion exchanger was stirred for a further 10 minutes with 0.1N ammonia solution (360 liters). Most of the nikkomicin activity was found in the second eluate. This eluate was concentrated by evaporating off the solvent under reduced pressure, and the residue was then lyophilized. The crude nikkomicin thus obtained was employed in the above Examples 1 to 6.

EXAMPLE 8

1 kg of basic ion exchanger [amino-methylated polystyrene (macroporous) crosslinked with 6% of divinylbenzene], which had first been washed with acetic acid and adjusted to pH 7.0, were added to 10 liters of culture broth (after separating off the mycelium and adjusting the pH value to 4.0 with acetic acid), while stirring.

The pH value of the solution was kept at 6.5 to 7.0 by adding acetic acid, and the suspension was stirred for one hour.

The loaded exchanger resin was then filtered off and extracted by stirring three times, in each case for 15 minutes and with in each case 1 liter of water. The washed ion exchanger resin was then extracted stepwise by stirring with in each case 1.5 liters of acetic acid of increasing concentration (1%, 2%, 3%, 4%, 5% and 10%), the pH value of the solution being kept constant during the particular extraction stage by adding acetic acid. 40 to 60% strength nikkomicin was obtained in a yield of 85%.

It will be appreciated that the instant specification and examples are set forth by way of illustration and not limitation, and that various modifications and changes may be made without departing from the spirit and scope of the present invention.

We claim:

1. A process for concentrating nikkomicins (X) and (Z) from a dilute impure aqueous solution thereof containing $\geq 0.5\%$ of a mixture of Nikkomicin (X) and (Z) comprising bringing the solution to a pH between about 4 and 7, with acetic acid, contacting the solution with a weakly basic ion exchanger selected from the group consisting of basic macroporous or gel-like polystyrene resins which are cross-linked with divinylbenzene and which are partly or completely substituted by primary, secondary, tertiary and quaternary nitrogen groups, basic macroporous or gel-like cross-linked polyacrylamides, basic macroporous or gel-like acrylates or methacrylates which are transamidated, basic macroporous aminomethylated polystyrene cross-linked with about 6% of divinylbenzene and basic gel-like dextrans, and eluting the adsorbed material with a lower aliphatic carboxylic acid thereby to obtain a concentrated mixture of nikkomicin (X) and nikkomicin (Z).

2. The process according to claim 1 in which the weakly basic ion exchanger is a macroporous aminomethylated polystyrene crosslinked with divinylbenzene.

3. A process according to claim 1, wherein the aqueous solution containing nikkomicin is brought to a pH between about 4 and 7 with acetic acid before adsorption onto the weakly basic ion exchanger.

4. A process according to claim 1, wherein the aqueous solution containing nikkomicin is brought to a pH between about 6 and 7 with acetic acid before adsorption onto the weakly basic ion exchanger.

5. A process according to claim 1, wherein acetic acid solutions of successively increasing concentrations are used for eluting the mixture of nikkomicin (X) and nikkomicin (Z) from the basic ion exchanger.

6. A process according to claim 1, wherein the aqueous solution of nikkomicin is pre-purified by adsorption onto an acid ion exchanger followed by elution with a weak base.

7. A process according to claim 6, wherein the solution which is pre-purified is a filtrate from the production of nikkomicin by microbial cultivation.

8. A process according to claim 6, wherein the nikkomicin in the pre-purified solution is isolated prior to treatment with the weakly basic ion exchanger.

9. A process according to claim 6, wherein the acid ion exchanger is a macroporous or gel-like ion exchanger of a polystyrene resin which is cross-linked with divinylbenzene and contains sulphonic acid groups.

10. A process according to claim 6, wherein the weak base for eluting the acid ion exchanger is dilute ammonia.

11. A process according to claim 1, wherein the dilute aqueous solution of nikkomicin which is contacted with the weakly basic ion exchanger is a culture filtrate directly from the production of nikkomicin by microbial cultivation without pre-purification.

12. A process according to claim 2, wherein the dilute aqueous solution is obtained by contacting a culture filtrate from the production of nikkomicin by microbial cultivation with a macroporous or gel-like acid ion exchanger of a polystyrene resin which is cross-linked with divinylbenzene and contains sulphonic acid groups thereby to adsorb the active material and eluting the active material therefrom with dilute ammonia, the resulting solution after adjustment to a pH between about 6 and 7 with acetic acid constituting the dilute impure aqueous solution which is contacted with the weakly basic ion exchanger, elution therefrom being effected with acetic acid solutions of successively increasing concentrations.

* * * * *